(12) United States Patent
Elison et al.

(10) Patent No.: US 11,529,364 B2
(45) Date of Patent: *Dec. 20, 2022

(54) SYNTHETIC COMPOSITION FOR TREATING METABOLIC DISORDERS

(71) Applicant: GLYCOM A/S, Hørsholm (DK)

(72) Inventors: Emma Elison, Hjärup (SE); Bruce McConnell, La Tour de Peilz (CH); Thierry Hennet, Otelfingen (CH); Louise Kristine Vigsnæs, København (DK)

(73) Assignee: Glycom A/S, Hørsholm (DK)

( * ) Notice: Subject to any disclaimer, the term of this patent is extended or adjusted under 35 U.S.C. 154(b) by 40 days.

This patent is subject to a terminal disclaimer.

(21) Appl. No.: 17/093,337

(22) Filed: Nov. 9, 2020

(65) Prior Publication Data

US 2021/0052615 A1    Feb. 25, 2021

Related U.S. Application Data

(63) Continuation of application No. 15/104,794, filed as application No. PCT/DK2015/050385 on Dec. 8, 2015, now Pat. No. 10,828,313.

(30) Foreign Application Priority Data

Dec. 8, 2014 (DK) .......................... PA 2014 70768

(51) Int. Cl.
| | |
|---|---|
| A61K 31/702 | (2006.01) |
| A61K 31/7012 | (2006.01) |
| A61K 31/7004 | (2006.01) |
| A61K 9/00 | (2006.01) |

(52) U.S. Cl.
CPC .......... *A61K 31/702* (2013.01); *A61K 9/0053* (2013.01); *A61K 31/7004* (2013.01); *A61K 31/7012* (2013.01)

(58) Field of Classification Search
CPC .. A61K 31/702; A61K 9/0053; A61K 1/7004; A61K 31/7012
USPC ............................................................ 514/61
See application file for complete search history.

(56) References Cited

U.S. PATENT DOCUMENTS

| | | | |
|---|---|---|---|
| 4,895,838 | A | 1/1990 | McCluer et al. |
| 5,906,982 | A | 5/1999 | Prieto et al. |
| 2011/0189149 | A1 | 8/2011 | Burcelin et al. |
| 2011/0256233 | A1 | 10/2011 | Fournell et al. |
| 2012/0171165 | A1 | 7/2012 | Buck et al. |
| 2012/0208782 | A1 | 8/2012 | Frantz |
| 2012/0294840 | A1 | 11/2012 | Newburg et al. |
| 2014/0037785 | A1 | 2/2014 | Barboza et al. |
| 2015/0010670 | A1 | 1/2015 | Mills et al. |
| 2016/0310514 | A1 | 10/2016 | Salomonsson et al. |

FOREIGN PATENT DOCUMENTS

| | | |
|---|---|---|
| EP | 0691079 A2 | 10/1996 |
| EP | 1332759 A1 | 8/2003 |
| WO | 2011096808 A1 | 8/2011 |
| WO | 2014/043330 A1 | 3/2014 |
| WO | 2014100696 A1 | 6/2014 |

OTHER PUBLICATIONS

Haarman et al. (Appl. Environ. Microbiol. 2005:71(5) pp. 2318-2324).*
Anatolltou, "Human Milk Benefits and Breastfeeding", Journal of Pediatric and Neonatoal Individualized Medicine, 2012; 1(1), pp. 11-18.
Asanuma et al., "Variation of Major Neutral Oligosaccharides Levels in Human Colostrum", European Journal of Clinical Nutrition, Apr. 2008, vol. 62, No. 4, pp. 488-494.
Kresser, "A Healthy Gut is the Key to Weight Loss", https://chriskresser.com/a-healthy-gut-is-the-hidden-key-to-weight-loss/, Oct. 29, 2010, pp. 1-3.
L. Lykouras et al., "Anxiety Disorders and Obesity", Psychiatriki, Oct.-Dec. 2011; 22(4):307-13, (abstract) p. 1.
David A. Fields et al., "A Narrative Review of the Associations Between Six Bioactive Components in Breast Milk and Infant Adiposity", Obesity, vol. 24 | No. 6 | Jun. 2016, pp. 1213-1221.
Stanley IP et al., "Breastfeeding and Maternal and Infant Health Outcomes in Developed Countries", AHRQ Publication No. 07-E007, Apr. 2007, pp. 1-415.
G. Gibson et al., "The International Scientific Association for Probiotics and Prebiotics (ISAPP) consensus statement on the definition and scope of prebiotics", Nature Reviews | Gastroenterology & Hepatology, vol. 14, Aug. 2017, pp. 491-502.

(Continued)

*Primary Examiner* — Shaojia A Jiang
*Assistant Examiner* — Michael C Henry
(74) *Attorney, Agent, or Firm* — Tom Biscoe; Kunzler Bean & Adamson

(57) ABSTRACT

A method for treating metabolic disorders in non-infant includes administering to an obese non-infant human during a treatment period an effective amount of a mixture of two or more synthetic neutral human milk oligosaccharides (HMOs) selected from 2'-fucosyllactose (2'FL), 3-fucosyllactose (3-FL), difucosyllactose (DFL), lacto-N-fucopentaose I (LNFP-I), lacto-N-tetraose (LNT), and lacto-N-neotetraose (LNnT), and optionally one or more excipients. The method further includes increasing in the gastrointestinal microbiota of the non-infant human during the treatment period, the relative abundance of *Bifidobacterium adolescentis* and reducing in the non-infant human during the treatment period, a precursor condition for a metabolic disorder associated with development of one or more of obesity-induced pre-diabetes and type 2 diabetes, the precursor condition selected from gut permeability, metabolic endotoxemia, low-grade metabolic inflammation, and body fat percentage.

20 Claims, No Drawings

(56) References Cited

OTHER PUBLICATIONS

R. Rosmond et al., "The hypothalamic-pituitary-adrenal axis activity as a predictor or cardiovascular disease, type 2 diabetes and stroke" Journal of Internal Medicine 2000, 247; pp. 188-1979 (Year 2000).
R. Silvennoinen et al., "Acute Psychological Stress Accelerates Reverse Cholesterol Transport Via Corticosteroid-Dependent Inhibition of Intestinal Cholesterol Absorption", Circulation Stress 2012, 111(11) pp. 1459-1469 (Year 2012).
L. Deveza et al. "Therapeutic Angiogenesis for Treating Cardiovascular Diseases", Theranostics 2012 2(8), pp. 801-814 (Year 2012).
Barile et al.,"Human milk and related oligosaccharides as prebiotics", Current Opinion in Biotechnology, 2013, pp. 1-6, sciencedirect.com.
Druart et al., "Modulation of the Gut Microbiota by Nutrients with Prebiotic and Probiotic Properties", Proceedings of the IUNS 20th International Congress of Nutrition (Part 2), 2014, pp. 1-10, American Society for Nutrition.
P. Cani et al., "Metabolic endotoxemia initiates obesity and insulin resistance", Diabetes, vol. 56, Jul. 2007, pp. 1761-1772.
Olivia Ballard et al., "Human Milk Composition: Nutrients and Bioactive Factors", National Institutes of Health, Pediatr Clin North Am, Feb. 1, 2014, pp. 1-24.
Undurti N. Das, "Breastfeeding prevents type 2 diabetes mellitus: but, how and why?", known about and downloaded from https://academic.oup.com/ajcn/article-abstract/85/5/1436/4633161 on Nov. 12, 2019, pp. 1-2.
David A. Sela et al, "Nursing our microbiota: molecular linkages between bifidobacteria and milk oligosaccharides", National Institutes of Health, Trends Microbiol, Jul. 1, 2011, pp. 1-18.
J. Chen et al., "Bifidobacterium adolescentis supplementation ameliorates visceral fat accumulation and insulin sensitivity in an experimental model of the metabolic syndrome", British Journal of Nutrition Sep. 14, 2011, 107, 1429-1434.
M. Joossens et al., "Dysbiosis of the faecal microbiota in patients with Crohn's disease and their unaffected relatives", Downloaded from gut.bmj.com on Aug. 22, 2011, pp. 631-637.
D. Guyonne et al. "Effect of a fermented milk containing Bifidobacterium animalis DN-173 010 on the health-related quality of life and symptoms in irritable bowel syndrome in adults in primary care: a multicentre, randomized, double-blind, controlled trial", Alimentary Pharmacology & Therapeutics. Apr. 26, 2007, pp. 475-486.
P.J. Whorewll et al, "Efficcy of an Encasulated Probiotic Bifidobacterium infantis 35624 in Woman with Irritable Bowel Syndrome", American Journal of Gastroenterology, 2006, pp. 1581-1590.
S. Duranti et al., "Genomic Characterization and Transcriptional Studies of the Starch-Utilizing Strain Bifidobacterium adolescentis 22L", Applied and Environmental Microbiology, vol. 80 No. 19, Oct. 2014, pp. 6080-6090.
A.M. Zivkovic, "Human milk glycobiome and its impact on the infant gastrointestinal microbiota", PNAS | Mar. 15, 2011 | vol. 108 | suppl. 1 | pp. 4653-4658.
J.S. Frick et al., "Identification of Commensal Bacterial Strains That Modulate Yersinia enterocolitica and Dextran Sodium Sulfate-Induced Inflammatory Responses: Implications for the Development of Probiotics", Infection and Immunity, American Society for Microbiology, vol. 75, No. 7, Jul. 2007, pp. 3490-3497.
T. Pozo-Rubio et al., "Immunostimulatory effect of faecal Bifidobacterium species of breast-fed and formula-fed infants in a peripheral blood mononuclear cell/Caco-2 co-culture system", British Journal of Nutrition, 106, May 31, 2011, p. 1216-1223.
R. Martin et al., "Isolation of Bifidobacteria from Breast Milk and Assessment of the Bifidobacterial Population by PCR-Denaturng Gradient Gel Electrophoresis and Quantitative Real-Time PCR", Applied and Environmental Microbiology, vol. 75, No. 4, Feb. 2009, pp. 965-969.
G.V. Coppa et al., "Oligosaccharides in 4 Different Milk Groups, Bifidobacteria, and Ruminococcus obeum", JPGN, vol. 53, No. 1, Jul. 2011, pp. 80-87.
A. Wittmann et al., "Plasmacytoid Dendritic Cells are Crucial in Bifidobacterium adolescentis-Mediated Inhibition of Yersinia enterocolitica Infection", PLOS, vol. 8, No. 8, Aug. 2013, pp. 1-10.
P. Wacklin et al., "Secretor Genotype (FUT2 gene) is Strongly Associated with the Composition of Bifidobacteria in the Human Intestine", PLOS, vol. 6 No. 5, May 2011, pp. 1-10.
C. Hoarau et al., "Supernatant of Bifidobacterium breve induces dendritic cell maturation, activation, and survival through a Toll-like receptor 2 pathway", J Allergy Clin Immunol, vol. 117, No. 3, Mar. 2006, pp. 696-702.
L. Chen, "Therapeutic effects of four strains of probiotics on experimental colitis in mice", World J Gastroenterol Jan. 21, 2009; 15(3): pp. 321-327.
E. Elison et al., "Oral supplementation of healthy adults with 2!-O-fucosyllactose and lacto-N-neotetraose is well tolerated and shifts the intestinal microbiota", British Journal of Nutrition, Aug. 22, 2016, pp. 1-13.
U.S. Appl. No. 15/183,431 "Office Action Summary", dated Oct. 6, 2020, pp. 1-35.
D. Tanne et al., "Body Fat Distribution and Long-Term Risk of Stroke Mortality", America Heart Association Journal, Feb. 14, 2005, pp. 1021-1025.
S. Kenchaiah et al., "Obesity and the risk of heart failure", The New England Journal of Medicine, vol. 347, No. 5, Aug. 1, 2002, pp. 305-313.

\* cited by examiner

SYNTHETIC COMPOSITION FOR TREATING METABOLIC DISORDERS

CROSS-REFERENCES TO RELATED APPLICATIONS

This is a continuation application of U.S. patent application Ser. No. 15/104,794 and claims priority to U.S. patent application Ser. No. 15/104,794 filed Dec. 8, 2015 which is the US national stage of PCT/DK2015/050385 which claims priority to DK application PA 2014 70768 the entire contents of each are incorporated herein by reference for all purposes as permissible by law.

FIELD

This invention relates generally to compositions and methods for the treatment of metabolic disorders such as obesity and obesity induced pre-diabetes and type 2 diabetes.

BACKGROUND

Diabetes type 2 is a metabolic disorder that is characterized by hyperglycaemia due to insulin resistance and relative lack of insulin and that is a rapidly growing global epidemic. The International Diabetes Federation (IDF) reports that as of 2013 there were more than 382 million people living with diabetes, and a further 316 million with impaired glucose tolerance who are at high risk from the disease (IDF Diabetes Atlas, $6^{th}$ edn.). The World Health Organization (WHO) furthermore estimates that 90 percent of people around the world who suffer from diabetes suffer from type 2 diabetes. Long-term complications from high blood sugar can include heart disease, strokes, diabetic retinopathy, kidney failure, and poor blood flow in the limbs.

Since it is unlikely that there has been a dramatic alteration in genetic factors in the past decades, environmental factors must play a key role in the rapid rise in diabetes. Gut microbiota has been proposed as a key factor (Burcelin et al. *Frontiers in Bioscience* 14, 5107 (2009)) with populations showing marked differences between healthy, obese, and type 2 diabetic patients (Bäckhed et al. *PNAS* 101, 15718 (2004), Qin et al. *Nature* 490, 55 (2012)). The dysbiosis of gut microbiota has the potential to affect host metabolism and energy storage (Ley et al. *Nature* 444, 1022 (2006)) and to affect gut permeability and, as a consequence, give rise to metabolic endotoxemia and higher plasma lipopolysaccharide (LPS). In addition, gut peptides such as glucagon-like peptide 1 (GLP1) and GLP2 can play key roles in these processes (Tremaroli et al. *Nature* 489, 242 (2012)). For example, GLP2, which is secreted by intestine L cells, is a key regulator of intestinal permeability (Cani et al. *Gut* 58, 1091 (2009)). Therapeutic regimes that target intestinal microbiota and intestinal barrier therefore show a broad prospect in treating diabetes (Kootte et al. *Diabetes, Obesity & Metabolism* 14, 112 (2012)).

Recent insights suggest that an altered composition and diversity of gut microbiota could play an important role in the development of metabolic disorders such as obesity and diabetes. Gut microbiota does not only participate in whole-body metabolism by affecting energy balance (Bäckhed et al. *PNAS* 101, 15718 (2004), Turnbaugh et al. *Nature* 444, 1027 (2006)) and glucose metabolism (Cani et al. *Diabetes* 57, 1470 (2008), Cani et al. *J. Endocrinol.* 185, 457 (2005)) but is also involved in development of the low-grade inflammation (Cani et al. *Diabetes* 57, 1470 (2008), Cani et al. *Gut* 58, 1091 (2009), Cani et al. *Diabetes* 56, 1761 (2007)) associated with obesity and related metabolic disorders such as diabetes. The association between inflammation and type 2 diabetes was described already in the 1950s, when epidemiological studies showed a rise in acute-phase response proteins in serum of type 2 diabetic patients compared with controls (Fearnley et al. *Lancet* 274, 1067 (1959), Ogston et al. *Lancet* 284, 1205 (1964)). Later, a specific link between inflammatory and metabolic responses was made with the discovery that compared with lean tissue, obese adipose tissue secretes inflammatory cytokines and that these inflammatory cytokines themselves can inhibit insulin signalling (Hotamisligil et al. *Science* 271, 665 (1996)). The definitive proof of a connection between inflammatory mediators and insulin resistance in obesity and type 2 diabetes came from genetic studies that interfered with inflammatory mediators and demonstrated beneficial effects of this interference on insulin action (Uysal et al. *Nature* 389, 610 (1997)).

In recent years, gut microbiota derived LPS has been shown to be involved in the onset and progression of inflammation, and in pathological situations, such as obesity and type 2 diabetes, LPS play a major role in the onset of disease (Cani et al. *Diabetes* 57, 1470 (2008), Cani et al. *Diabetes* 56, 1761 (2007)). After only one week of a high-fat diet in mice, commensal intestinal bacteria are translocated from the intestine into adipose tissue and the blood where they can induce inflammation (Amar et al. *EMBO Mol. Med.* 3, 559 (2011)). This metabolic bacteraemia is characterized by an increased co-localization with dendritic cells from the intestinal lamina propria and by an augmented intestinal mucosal adherence of non-pathogenic *Escherichia coli*. The bacterial translocation process from intestine towards tissue with resulting inflammation was reversed by six weeks of treatment with the probiotic strain *Bifidobacterium animalis* subsp. *lactis* 420, suggesting an involvement of the microbiota.

EP-A-1332759 discloses that oral doses of 2'-FL, 3'-SL, 6'-SL, LNnT and sialic acid promote insulin secretion in type 2 diabetes-model mice.

EP-A-2143341 discloses that a mixture of GOS, sialylated oligosaccharides and N-acylated oligosaccharides reduces triglyceride concentration in liver in model mice.

EP-A-2332552 discloses that 3'-SL and 6'-SL reduce/prevent fat accumulation in the liver and other organs in high-fat diet mice and rats.

WO 2013/057061 discloses a composition for increasing insulin sensitivity and/or reducing insulin resistance. The composition contains long chain polyunsaturated fatty acids, probiotics and a mixture of oligosaccharides containing at least one of lacto-N-neotetraose (LNnT) and lacto-N-tetraose (LNT), at least one N-acetylated oligosaccharide different from LNnT and LNT, at least one sialylated oligosaccharide and at least one neutral oligosaccharide, for use in increasing insulin sensitivity and/or reducing insulin resistance. This composition can also contain 2'-O-fucosyllactose (2'-FL). The composition is particularly adapted for use in infants who were born preterm and/or who experienced IUGR, and in pregnant women suffering from gestational diabetes. It is also stated that the composition can be given to children, adolescents, and adults suffering from insulin resistance and/or type II diabetes. It is stated that the efficacy of the composition can be the result of the synergistic combination of immunity modulator effects triggered by the probiotics and the LC-PUFA through their stimulation with the specific oligosaccharide mixture.

Most current therapeutic approaches aim at treating the consequences rather than causes of the impaired metabolism. This strategy is not efficient and therefore, there has remained a need for therapies that reduce intestinal permeability, endotoxemia and low-grade inflammation in patients with metabolic disorders to improve glucose and insulin sensitivity, and which are safe with little or no adverse side effects.

SUMMARY

In one aspect, this invention provides a synthetic composition for use in one or more of the following:
reducing intestinal permeability,
reducing endotoxemia,
reducing low-grade inflammation,
reducing body fat percentage,
increasing the abundance of bifidobacteria, and/or
increasing the levels of the gut hormones GLP-1 and GLP-2,
in a patient having a metabolic disorder, for example obesity, obesity induced pre-diabetes and obesity induced type 2 diabetes, characterized in that the synthetic composition contains an effective amount of one or more human milk monosaccharides or one or more human milk oligosaccharides ("HMOs") or both. The synthetic composition is preferably a nutritional composition. The composition can further comprise a source of threonine, serine and/or proline. Preferably the human milk oligosaccharides include both fucosylated and core HMOs such as LNT and LNnT HMOs. The human milk oligosaccharides can also include sialylated HMOs. Alternatively, the human milk oligosaccharides include both fucosylated and sialylated HMOs and the human milk oligosaccharides can also include backbone HMOs such as LNT and LNnT. The patient can be a paediatric or adult patient, preferably a prepubescent child.

In another aspect, this invention provides a method for one or more of the following:
reducing intestinal permeability,
reducing endotoxemia,
reducing low-grade inflammation,
reducing body fat percentage,
increasing the abundance of bifidobacteria, and/or
increasing the levels of the gut hormones GLP-1 and GLP-2,
in a patient having a metabolic disorder, for example obesity, obesity induced pre-diabetes and obesity induced type 2 diabetes, the method comprising orally administering to the patient an effective amount of one or human milk monosaccharides or one or more human milk oligosaccharides, or both, preferably in the form of a synthetic composition. The patient can be a paediatric or adult patient, preferably a prepubescent child.

In a further aspect, this invention relates to a use of one or more human milk monosaccharides or one or more human milk oligosaccharides or both, preferably in the form of a synthetic composition, for one or more of the following:
reducing intestinal permeability,
reducing endotoxemia in a patient,
reducing low-grade inflammation,
reducing body fat percentage,
increasing the abundance of bifidobacteria, and/or
increasing the levels of the gut hormones GLP-1 and GLP-2,
in a patient having a metabolic disorder, for example obesity, obesity induced pre-diabetes and obesity induced type 2 diabetes. The patient can be a paediatric or adult patient, preferably a prepubescent child.

It has been surprisingly found that human milk monosaccharides, advantageously sialic acid and/or fucose, and human milk oligosaccharides, advantageously 2'-FL, 3-FL, LNT, LNnT, 3'-SL, 6'-SL, DFL, DSLNT and/or LNFP-I, not only modulate inflammation and microbiota in the GI tract, but also decrease gut permeability, reduce endotoxemia and low-grade inflammation, improve body composition (by reducing body fat percentage), increase the abundance of bifidobacteria, and increase the levels of the gut hormones GLP-1 and GLP-2 in human patients. Preferably the abundance of *Bifidobacteria adolescentis* is increased. This can result in lower chronic inflammation, improved insulin sensitivity and reduced insulin resistance. Obese and pre-diabetic patients can be stabilized and the progression to diabetes slowed, stopped or reversed. Diabetic patients can be stabilized or at least the progression to diabetes with complications slowed.

In all aspects disclosed above the synthetic composition preferably contains one or more core HMOs and/or one or more fucosylated HMOs, more preferably one or more core HMOs and one or more fucosylated HMOs. Even more preferably the core HMO is selected from the group consisting of LNT, LNnT, LNH, LNnH and pLNnH, particularly LNT and LNnT, and the fucosylated HMO is selected from the group consisting of 2'-FL, 3-FL, DFL and LNFP-I, particularly 2'-FL. Advantageously, the synthetic composition contains 2'-FL and LNT and/or LNnT.

DETAILED DESCRIPTION OF THE INVENTION

The term "patient" preferably means a human that can be a paediatric or adult patient. However, a "patient" can also be any other mammal.

The term "oral administration" preferably means any conventional form for the oral delivery of a composition to a patient that causes the deposition of the composition in the gastrointestinal tract (including the stomach) of the patient. Accordingly, oral administration includes swallowing of composition by the patient, enteral feeding through a naso-gastric tube, and the like.

The term "effective amount" preferably means an amount of a composition that provides a human milk monosaccharide or human milk oligosaccharide in a sufficient amount to render a desired treatment outcome in a patient. An effective amount can be administered in one or more doses to the patient to achieve the desired treatment outcome.

The term "human milk monosaccharide" or "HMS" preferably means a monosaccharide found in human breast milk. Examples include sialic acid and L-fucose. In human milk, the sialic acid is N-acetylneuraminic acid.

The term "human milk oligosaccharide" or "HMO" preferably means a complex carbohydrate found in human breast milk that can be in acidic or neutral form. More than about 200 different HMO structures are known to exist in human breast milk (Urashima et al.: Milk Oligosaccharides, Nova Biomedical Books, New York, 2011). HMOs can be core, fucosylated and sialylated oligosaccharides. Core HMOs consist of Glu, Gal and GlcNAc and are devoid of Fuc and sialic acid. Examples of core HMOs include lacto-N-tetraose (LNT), lacto-N-neotetraose (LNnT), lacto-N-neohexaose (LNnH), lacto-N-hexaose (LNH) and p-lacto-N-neohexaose (pLNnH). Fucosyl HMOs are fucosylated lactoses or fucosylated core HMOs such as 2'-fucosyllactose (2'-FL), lacto-N-fucopentaose I(LNFP-I), lacto-N-difucohexaose I (LNDFH-I), 3-fucosyllactose (3-FL), difucosyl-lactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH). Sialyl HMOs are sialylated lactoses or sialylated core HMOs such as 3',6-disialyllacto-N-tetraose (DSLNT), 6'-sialyllactose (6'-SL), 3'-sialyllactose (3'-SL), 6'-sialyllacto-N-neotetraose (LST c), 3'-sialyllacto-N-tetraose (LST a) and 6-sialyllacto-N-tetraose (LST b). HMOs containing both sialyl and fucosyl groups may be considered to belong to either of the latter two groups. Examples for sialylated and fucosylated HMOs include disialyl-fucosyl-lacto-N-hexaose II (DSFLNH-II), fucosyl-sialyl-lacto-N-neohexaose I (FSLNnH-I), fucosyl-sialyl-lacto-N-hexaose I (FSLNH-I) and 3-fucosyl-3'-sialyl-lactose (FSL).

The term "intestinal permeability" preferably means the permeability of the intestinal mucosa of a patient, permitting the absorption of vital nutrients from the gut lumen while presenting a barrier against the passage of pathogenic substances into the patient's body.

The term "endotoxemia" preferably means the presence of endotoxins, such as gut microbiota-derived lipopolysaccharides (LPS) in the blood of a patient.

The term "low-grade inflammation" preferably means an immune system response of a patient characterized by altered levels of pro-inflammatory and anti-inflammatory cytokines as well as numerous other markers of immune system activity in response to an injurious stimuli.

Body fat percentage preferably means total mass of body fat divided by total mass of the body.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified E. coli.

The human milk monosaccharides and/or oligosaccharides can be in the form of one or more core HMOs and one or more fucosylated HMOs. Alternatively one or more core HMOs and one or more sialylated HMOs can be used. In a further alternative, one or more fucosylated HMOs and one or more sialylated HMOs can be used. In a preferred embodiment, one or more core HMOs, one or more sialylated HMOs and one or more fucosylated HMOs are used.

The term "glycaemic index" or "GI" is defined as the incremental area under the two-hour blood glucose response curve (AUC) following a 12-hour fast and ingestion of a food with a certain quantity of available carbohydrate (usually 50 g). The AUC of the test food is divided by the AUC of the standard (glucose, the standard, has a GI of 100) and multiplied by 100. The average GI value is calculated from data collected in 10 human subjects. Both the standard and test food must contain an equal amount of available carbohydrate. The result gives a relative ranking for each tested food. Tables reporting commonly accepted GI values for a variety of foods are available including the international GI database maintained by the University of Sydney, and available on the internet at: www.glycemicindex.com.

The synthetic composition can take any suitable form. For example, the composition can be in the form of a nutritional composition which contains other macronutrients such as proteins, lipids or other carbohydrates. The synthetic composition can also be a pharmaceutical composition.

Nutritional Compositions

A nutritional composition can contain sources of protein, lipids and/or digestible carbohydrates and can be in solid, powdered or liquid forms. The composition can be designed to be the sole source of nutrition or a nutritional supplement.

Suitable protein sources include intact, hydrolysed, and partially hydrolysed protein, which can be derived from any suitable source such as milk (e.g., casein, whey), animal (e.g., meat, fish), cereal (e.g., rice, corn), and vegetable (e.g., soy, potato, pea), insect (e.g., locust) and combinations of these sources. Examples of the source of protein include whey protein concentrates, whey protein isolates, whey protein hydrolysates, acid caseins, sodium casemates, calcium casemates, potassium casemates, casein hydrolysates, milk protein concentrates, milk protein isolates, milk protein hydrolysates, non-fat dry milk, condensed skim milk, soy protein concentrates, soy protein isolates, soy protein hydrolysates, pea protein concentrates, pea protein isolates, pea protein hydrolysates, collagen proteins, and combinations of these sources.

The amount of protein is preferably sufficient to provide about 5 to about 30% of the energy of the nutritional composition; for example about 10% to about 25% of the energy. Within these ranges, the amount of protein can vary depending upon the nutritional needs of the intended individual.

The nutritional compositions can also include free amino acids such as tryptophan, glutamine, tyrosine, methionine, cysteine, taurine, arginine, carnitine, threonine, serine and proline and combinations of these amino acids. Threonine, serine and proline are important amino acids for the production of mucin which aids gut barrier function.

Any suitable source of other carbohydrates can be used. Examples include maltodextrin, hydrolyzed or modified starch or corn starch, glucose polymers, corn syrup, corn syrup solids, rice-derived carbohydrates, sucrose, glucose, fructose, lactose, high fructose corn syrup, honey, sugar alcohols (e.g., maltitol, erythritol, sorbitol, etc.), isomaltulose, sucromalt, pullulan, potato starch, slowly-digested carbohydrates, dietary fibres such as oat fibre, soy fibre, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinogalactans, glucomannan, xanthan gum, alginate, pectin, low and high methoxy pectin, cereal beta-glucans (i.e., oat beta-glucan, barley beta-glucan), carrageenan and psyllium, Fibersol™, other resistant starches, and combinations of these carbohydrate.

Preferably the carbohydrate source includes low glycaemic index carbohydrates having a GI score of 55 or below. Examples of low glycaemic index carbohydrates include sucromalt, Fibersol™ (inulin), maltodextrins having a dextrose equivalence (DE) of less than 15, rice syrup having a dextrose equivalence of less than 15, fructooligosaccharides, resistant starches, starches, fruit sourced fibres, vegetable sourced fibres, whole grains, beta-glucans, soy fibres, oat fibres, locust bean gum, konjac flour, hydroxypropyl methylcellulose, gum acacia, chitosan, arabinogalactans, xanthan gum, alginate, low and high methoxy pectin, carrageenan, psyllium, isomaltulose, glycerine and sugar alcohols.

The nutritional compositions can include carbohydrates in an amount sufficient to provide about 30 to about 70% of the energy of the composition, for example about 35 to about 65% of the energy. Within these parameters, the amount of carbohydrate can vary widely.

Suitable lipid sources include coconut oil, fractionated coconut oil, soy oil, corn oil, olive oil, safflower oil, high oleic safflower oil, medium chain triglycerides, sunflower oil, high oleic sunflower oil, palm and palm kernel oils, palm olein, canola oil, marine oils, cottonseed oils and combinations of these oils. Fractionated coconut oils are a suitable source of medium chain triglycerides. The lipids can contain polyunsaturated fatty acids such as n-3 LC-PUFA. The n-3 LC-PUFA can be a C20 or a C22 n-3 fatty acid. Preferably the n-3 LC-PUFA is docosahexanoic acid (DHA, C22:6, n-3). The source of LC-PUFA can be, for example, egg lipids, fungal oil, low EPA fish oil or algal oil.

The nutritional compositions can include lipids in an amount sufficient to provide about 10 to about 50% of energy of the nutritional composition, for example about 15 to about 40% of the energy.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 μg/ml to about 10 μg/ml. Lutein can be included in an amount of from about 0.001 μg/ml to about 10 μg/ml, preferably from about 0.044 μg/ml to about 5 g/ml of lutein. Lycopene can be included in an amount from about 0.001 μg/ml to about 10 μg/ml, preferably about 0.0185 mg/ml to about 5 g/ml of lycopene. Beta-carotene can comprise from about 0.001 μg/ml to about 10 mg/ml, for example about 0.034 μg/ml to about 5μg/ml of beta-carotene. The nutritional composition can also include a source of anthocyanidins. This can be in the form of a fruit or a fruit extract. Particularly useful fruits and fruit extracts include plum/prune, apple, pear, strawberry, blueberry, raspberry, cherry, and their combinations.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HNO19, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilizers, lubricants, and so forth.

The nutritional composition can be in the form of a food, soluble powder, a liquid concentrate, or a ready-to-use formulation. The composition can be eaten, drunk or can be fed via a nasogastric. Various flavours, fibres, and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively the composition can be spray-dried and processed and packaged as a reconstitutable powder.

The nutritional composition can also be in the form of a food such as a nutritional bar, a yoghurt, etc. These forms can be produced using standard technologies and processes.

When the nutritional product is a ready-to-feed nutritional liquid, the total concentration of HMSs/HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMSs/HMOs in the liquid, by weight of the liquid, is from about 0.0002% to about 4.0%, including from about 0.002% to about 3.0%, including from about 0.02% to about 2.0%.

Unit Dosage Forms

The synthetic composition of this invention can also be in a unit dosage form such as a capsule, tablet or sachet. For example, the composition can be in a tablet form comprising the human milk monosaccharides and/or oligosaccharides, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione. The unit dosage forms, especially those in sachet form, can also include various nutrients including macronutrients.

Administration Dosing

For reducing intestinal permeability, endotoxemia, low-grade inflammation and/or body fat percentage, and/or increasing the abundance of bifidobacteria and/or the levels of the gut hormones GLP-1 and GLP-2 in a person, the amount of human milk mono and/or oligosaccharide(s) required to be administered to the person will vary depending upon factors such as the risk and condition severity, the age of the person, the form of the composition, and other medications being administered to the person. However, the required amount can be readily set by a medical practitioner and would generally be in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day. An appropriate dose can be determined based on several factors, including, for example, the body weight and/or condition of the patient being treated, the severity of the condition, being treated, other ailments and/or diseases of the person, the incidence and/or severity of side effects and the manner of administration. Appropriate dose ranges can be determined by methods known to those skilled in the art. During an initial treatment phase, the dosing can be higher (for example 200 mg to 20 g per day, preferably 500 mg to 15 g per day, more preferably 1 g to 10 g per day, in certain embodiments 2.5 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g per day).

A synthetic composition of this invention can be co-administered to a patient who is also receiving a standard-of-care medication for obesity or diabetes.

EXAMPLES

Examples are now described to further illustrate the invention:

Example 1

Treating High Fat Diet Induced Obesity and Diabetes 10-week-old C57BL/6J mice (120 mice) are housed in groups of five mice per cage, with free access to food and water. The mice are divided into 12 groups of 10 mice, one control group and 11 treatment groups. All of the mice are fed a high-fat (HF) diet (60% fat and 20% carbohydrates [kcal/100 g], or an HF diet supplemented with HMS/HMO (20 g/kg of diet) for 8 weeks. Food and water intake are recorded twice a week. The 11 treatment groups are each administered one of the following: a) sialic acid, b) L-fucose, c) 2'-FL, d) 3-FL, e) 3'-SL, f) 6'-SL, g) LNT, h) LNnT, i) LNFP-I, j) DSLNT and k) a combination of these saccharides. The control group is administered the HF diet only. Fresh food is given daily.

Intraperitoneal or oral glucose tolerance tests are performed as follows: 6-h-fasted mice are injected with glucose into the peritoneal cavity (1 g/kg glucose, 20% glucose solution) or by gavage (3 g/kg glucose, 66% glucose solution). Blood glucose is determined with a glucose meter (Roche Diagnostics) on 3.5 µl blood collected from the tip of the tail vein. A total of 20 µl blood is sampled 30 min before and 15 or 30 min after the glucose load to assess plasma insulin concentration.

To assess intestinal permeability in vivo, the intestinal permeability of 4000 Da fluorescent dextran-FITC (DX-4000-FITC) is measured. Mice are fasted for 6 h before given DX-44-FITC by gavage (500 mg/kg body weight, 125 mg/ml). After 1 h and 4 h, 120 ml of blood is collected from the tip of the tail vein. The blood is centrifuged at 4° C., 12 000 g for 3 min. Plasma is diluted in an equal volume of PBS (pH 7.4) and analysed for DX-4000-FITC concentration with a fluorescence spectrophotometer at an excitation wavelength of 485 nm and emission wavelength of 535 nm. Standard curves are obtained by diluting FITC-dextran in non-treated plasma diluted with PBS (1:3 v/v).

Plasma LPS, cytokines and gut hormones are determined as follows. Plasma LPS concentration is measured using a kit based upon a Limulus amoebocyte extract (LAL kit endpoint-QCL1000). Samples are diluted 1/40 to 1/100 and heated for 20 cycles of 10 min at 68° C. and 10 min at 4° C. An internal control for LPS recovery is included in the calculation. Plasma cytokines (interleukin (IL) 1α, IL 1β, tumour necrosis factor (TNF)α, IL6, monocyte chemoattractant protein (MCP)-1, macrophage inflammatory protein (MIP)-1α, IL10, interferon (INF) c, IL15, IL18) and gut hormones (GLP-1 (active), GIP (total), amylin (active), pancreatic polypeptide) are respectively determined in duplicate by using a Bio-Plex Multiplex kit, or a mouse gut hormones panel (LincoPlex), and measured by using Luminex technology, an EIA kit (GLP-2 EIA kit) is used to quantify GLP-2.

Mice are anaesthetised (ketamine/xylazine, intraperineally, 100 and 10 mg/kg, respectively) after a 5 h period of fasting, and blood samples and tissues are harvested for further analysis. Mice are killed by cervical dislocation. Liver, caecum (full and empty), muscles (vastus lateralis), and adipose tissues (mesenteric and corresponding lymph nodes, epididymal, subcutaneous and visceral) are precisely dissected and weighed. The intestinal segments (jejunum, colon) are immersed in liquid nitrogen, and stored at −80° C., for further analysis.

To assess the microbiota profile, the caecal contents collected post mortem from mice are stored at −80° C. DNA is isolated from the caecal content samples using QIAamp DNA Stool Mini Kit. The DNA concentration of extracts is measured using NanoDrop. Aliquots of 100 ng of extracted DNA are subjected to PCR using the 16S rDNA universal heteroduplex analysis (HDA) primers HDA1-GC 50-CGCCCGGGGCGCGCCCCGGGCGGGGCGGGGGC ACGGGGGGACTCCTACGGGAGGCAGCAGT-30 and HDA2 50-TTACCGCGGCTGCTGGCA-30 (both primers are disclosed in Walter et al. *Appl. Environ. Microbiol.* 66, 297 (2000)) at 56° C. for strand annealing. Initial denaturation at 94° C. for 4 min is followed by thirty cycles of 30 s at 94° C., 30 s at 56° C. and 1 min at 72° C. The quality of PCR products is verified by agarose gel electrophoresis.

Amplified 16S rDNA fragments are separated by denaturing gradient gel electrophoresis (DGGE) using an INGENY-phorU system equipped with 6% polyacrylamide gels with a denaturant in the range of 30-55%, where 100% denaturant is equivalent to 7M-urea and 40% formamide. Electrophoresis is carried out at 130 V for 4-5 hours at 60° C. Polyacrylamide gels are stained with GelRede nucleic acid stain for 45 min, destained in ultrapure water and viewed under UV light. Bands of interest are excised from gels and lysed in ultrapure water. Extracted DNA is re-amplified using the same primers and PCR conditions. To purify the bacterial DNA, PCR products are reloaded on a denaturant gradient gel followed by excision and lysis of selected bands. DNA samples recovered from lysed bands of the second DGGE are re-amplified by PCR before purification using the QIAquick PCR Purification Kit and sequenced. Species identification is done using the Ribosomal Microbiome Database Project Classifier tool. Because of the limited sensitivity of DGGE to quantify microbial diversity, the microbial composition of DNA samples is also analysed using high-throughput sequencing. The V5-V6 region of 16S rRNA from caecal content DNA samples is amplified using the primers 784F 50-AGGATTAGATACCCT-GGTA-30 and 1061R 50-CRRCACGAGCTGACGAC-30 3640 (both primers are disclosed in Andersson et al. *PloS ONE* 3, e2836 (2008)). Amplicons are pyrosequenced using a Roche 454 GS-FLX system. Sequences of at least 240 nucleotides and containing no more than two undetermined bases are retained for taxonomic assignment. The QIIME software is used for chimera check and the Greengenes database is used for classification. Bacterial diversity is determined at the phylum, family and genus levels.

To assess bacterial translocation from intestine into tissues, mesenteric adipose tissue (MAT) and corresponding lymph nodes (MLN) are harvested, and luminal and mucosal contents of each intestinal segment separated. Quantification of bacterial DNA is performed by isolating genomic DNA from blood, MAT, MLN or intestine (contents and mucosa). All bacterial DNA is quantified by quantitative real-time PCR targeting conserved regions of the 16S rRNA gene, with bacterial DNA as standard template for absolute quantification.

In order to assess barrier permeability, the expression of occludin and zonula occludens-1 (ZO-1) tight-junction proteins are assessed. Jejunum segments are immediately removed, washed with PBS, mounted in embedding medium, and stored at −80° C. until use. Cryosections (5 mm) are fixed in acetone at −20° C. for 5 min for occludin and in ethanol for 30 min at room temperature and in acetone at −20° C. for 5 min for ZO-1. Non-specific background is blocked by incubation with 10% bovine serum albumin (BSA) in Tris-buffered saline (TBS) and 0.3% Triton X-100 (30 min at room temperature). Sections are incubated with rabbit anti-occludin or rabbit anti-ZO-1 (1:400 for ZO-1 and 1:100 for occludin staining) for 2 h. Sections are washed three times for 10 min in TBS and probed with goat anti-rabbit fluorescein isothiocyante (FITC)-conjugated antibodies (1:50). Slides are washed three times for 10 min in TBS and mounted in mounting medium. Sections are visualized on a fluorescence microscope. As a control, slides are incubated with serial dilutions of the primary antibody to signal extinction. Two negative controls are used: slides incubated with irrelevant antibody or without primary antibody. All the stainings are performed in duplicate in non-serial distant sections, and analyzed in a double-blind manner by two different investigators.

The results show that HMS/HMO improve gut barrier function and reduce the metabolic inflammation and insulin resistance associated with obesity by increasing release of gut peptides, such as glucagon-like peptide-1 and -2 (GLP-1 and -2).

Example 2

Treating Obesity Induced Diabetes

Six-week-old ob/ob mice (120 mice) on C57BL/6 background are housed in a controlled environment (12 h daylight cycle) in groups of 2 mice/cage, and kept with free access to food and drinking water. The mice are separated into 12 groups of 10 mice, one control group and 11 treatment groups. One group is fed a control diet, and the 11 treatment groups each receive a control diets containing one of the following HMS/HMO (20 g/kg of diet) for five weeks: a) sialic acid, b) L-fucose, c) 2'-FL, d) 3-FL, e) 3'-SL, f) 6'-SL, g) LNT, h) LNnT, i) LNFP-I, j) DSLNT, and k) a combination of these saccharides. Fresh food is given daily.

Experiments to show impact of HMS/HMO on glucose tolerance, intestinal permeability plasma LPS, cytokines and gut hormones, caecal microbiota profile and bacterial translocation are performed as described under Example 1.

Example 3

Human Trial in Overweight and Obese Children

A total of 60 male and female patients, enrolled to a childhood obesity treatment program, are recruited to participate in the study. Patients are randomized into three groups, each of 20 patients, with 2 groups receiving different investigational products and one group receiving a placebo product for 8 weeks. The investigational products contain 4.5 grams of either 2'-FL alone or a combination of 2'-FL and LNnT while the placebo product contains 4.5 grams glucose. All products are in powder form in a unit dosage container.

The patients are eligible to participate if: they are between 5 and 10 years of age, have a BMI SDS of ≥2.0 and are enrolled in the childhood obesity treatment program at the Children's Obesity Clinic. All recruited patients and their representatives are able and willing to understand and comply with the study procedures. Patients are excluded if: they have participated in a clinical study one month prior to the screening visit and throughout the study; have any gastrointestinal disease(s) that may cause symptoms or may interfere with the trial outcome; have other severe disease(s) such as malignancy, kidney disease or neurological disease; have psychiatric disease; have used highly dosed probiotic supplements (yoghurt allowed) 3 months prior to screening and throughout the study; have consumed antibiotic drugs 3 months prior to screening and throughout the study; and consume on a regular basis medication that might interfere with symptom evaluation 2 weeks prior to screening and throughout the study.

At the initial visit (screening) patients and their representatives are given both oral and written information about the study; the children are asked for informed assent and their representatives to sign an informed consent form.

Eligibility criteria are checked and for children who are enrolled to the study, medical history and concomitant medication are registered. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences are measured and food intake is registered. Fasting blood samples are collected for safety and biomarker studies and for biobanking.

The serum from the blood samples is transferred to cryotubes and stored at −80° C. The following biomarkers are measured; Lipopolysaccharides (LPS), hsCRP, free fatty acids, total cholesterol, HDL, LDL, HbA1c, glucose, insulin, triglycerides, TNF-α, IL-1β, IL-6, IL-8, IL-10, GLP-1, GLP-2, Adiponectin, and Zonulin.

Equipment for collecting faecal samples is distributed. The faecal samples are stored at −80° C. until analysis. Microbiological analysis is performed on the faecal samples using 16S rRNA gene sequencing.

The Rome III Diagnostic Questionnaire for Paediatric Functional GI Disorders (QPFG) is completed on site by the participating child's representative(s), and the Bristol Stool Form Scales (B SFS) is distributed to the participant's representative(s) with instructions to assess the stool consistency at each faecal sampling point using the BSFS.

At the second visit (randomization), patients and their representatives are asked about adverse events, faecal samples are collected and equipment for collection of new samples is distributed. BSFS is collected and new BSFS is distributed. Study products are distributed together with a compliance form (diary). Patients and their representatives are reminded to follow the healthy dietary habits.

The study runs for 8 weeks with the patients consuming either a placebo or one of two investigational products daily. Patients are instructed to consume the products in the morning with breakfast. Compliance is monitored via a compliance form (diary) to be filled in daily.

Four weeks after commencement there is an intermediate check. Patients and their representatives are asked about adverse events and any changes in the patient's usual medication. Fecal samples are collected and equipment for collection of new samples is distributed. Blood pressure, pulse rate, waist and hip circumference, height and bodyweight are measured and BMI SDS calculated. The QPFG questionnaire is completed on site by the participating child's representative. The BSFS is collected and new BSFS is distributed to the participant's representative(s) with instructions to assess the stool consistency at each faecal sampling point using the BSFS. Patients and their representatives are reminded to follow the healthy dietary habits.

At the end of intervention (8 weeks), each patient has a visit with the medical team. Patients and their representatives are asked about adverse events and any changes in the patient's usual medication. Study products and compliance forms are collected to check compliance. BSFS and faecal samples are collected and equipment for collection of new samples is distributed. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking, and equipment for collecting faecal samples is distributed. The QPFG questionnaire is completed on site by the participating child's representative (s).

To examine potential long term effects of the intervention, an un-blinded follow-up period follows with a visit 8 weeks after end of intervention. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking. Fecal samples are collected. The intervention contributes to a normal body composition, and the patients given the investigational products show a greater reduction of body fat, body weight and BMI SDS as compared to the placebo group. The blood biomarker analysis indicates that the patients given the investigational products have increased levels of GLP-1 and GLP-2, reduced levels of metabolic endotoxemia and inflammatory markers and reduced gut permeability indicating an improved mucosal barrier compared to the placebo. The faecal analysis indicates that the patients given the investigational products have reduced bacterial dysbiosis and a higher level of bifidobacteria compared to the placebo, particularly *Bifidobacteria adolescentis*.

Example 4

Nutritional Composition

A ready to feed nutritional composition is prepared from water, maltodextrin, milk protein concentrate, Sucromalt, glycerine, cocoa powder, soy protein isolate, fructose, high oleic safflower oil, soy oil, canola oil, plant sterol esters, HMSs/HMOs, soy lecithin, magnesium chloride, calcium phosphate, carrageenan, sodium ascorbate, potassium citrate, sodium phosphate, calcium citrate, choline chloride, potassium chloride, sodium citrate, magnesium oxide, taurine, L-carnitine, alpha-tocopheryl acetate, zinc sulphate, ferrous sulphate, niacinamide, calcium pantothenate, vitamin A palmitate, citric acid, manganese sulphate, pyridoxine hydrochloride, vitamin D3, copper sulphate, thiamine mononitrate, riboflavin, beta carotene, folic acid, biotin, potassium iodide, chromium chloride, sodium selenate, sodium molybdate, phytonadione, vitamin B12.

The composition has an energy density of 0.8 kcal/ml with an energy distribution (% of kcal) as follows: protein: 20%, carbohydrate: 48%, fat: 32%.

Example 5

Tablet Composition

A tablet is prepared from HMS/HMO, hydroxypropyl methylcellulose, sodium alginate, gum, microcrystalline cellulose, colloidal silicon dioxide, and magnesium stearate. All raw materials except the magnesium stearate are placed into a high shear granulator and premixed. Water is sprayed onto the premix while continuing to mix at 300 rpm. The granulate is transferred to a fluidized bed drier and dried at 75° C. The dried powder is sieved and sized using a mill. The resulting powder is then lubricated with magnesium stearate and pressed into tablets. The tablets each contain 325 mg of HMS/HMO. The tablets each have a weight of 750 mg.

Example 6

Capsule Composition

A capsule is prepared by filling about 1 g of HMS/HMO into a 000 gelatine capsule using a filing machine. The capsules are then closed. The HMS/HMO are in free flowing, powder form.

What is claimed is:

1. A method comprising:
    administering to an obese non-infant human during a treatment period an effective amount of a single synthetic fucosylated human milk oligosaccharide (HMO) selected from 2'-fucosyllactose (2'-FL), 3-fucosyllactose (3-FL), difucosyllactose (DFL), and lacto-N-fucopentaose I (LNFP-I), and optionally one or more excipients;
    increasing in the gastrointestinal microbiota of the non-infant human during the treatment period, the relative abundance of *Bifidobacterium adolescentis*; and
    reducing in the non-infant human during the treatment period, a precursor condition for a metabolic disorder associated with development of one or more of obesity-induced pre-diabetes and type 2 diabetes, the precursor condition selected from gut permeability, metabolic endotoxemia, low-grade metabolic inflammation, and body fat percentage.

2. The method of claim 1, wherein the reduced precursor condition for the metabolic disorder associated with development of the one or more of obesity-induced pre-diabetes and type 2 diabetes is gut permeability.

3. The method of claim 1, wherein the reduced precursor condition for the metabolic disorder associated with development of the one or more of obesity-induced pre-diabetes and type 2 diabetes is body fat percentage.

4. The method of claim 1, further comprising increasing, in the gastrointestinal tract of the non-infant human, a level of glucagon-like peptide selected from GLP-1 and/or GLP-2 relative to the level of the selected glucagon-like peptide prior to administering the single HMO.

5. The method of claim 1, wherein:
    the treatment period comprises an initial treatment phase and a maintenance phase;
    the effective amount of the selected HMO is from about 2.5 g to about 7.5 g daily during the initial treatment phase; and
    the effective amount of the selected HMO is from about 1 g to about 2.5 g daily during the maintenance phase.

6. The method of claim 1, wherein single synthetic HMO is administered in a unit dosage form.

7. The method according to claim 1, wherein the obese non-infant human is a prepubescent child.

8. A method comprising:
    administering to an obese non-infant human during a treatment period an effective amount of a single synthetic nonfucosylated human milk oligosaccharide (HMO) selected from lacto-N-tetraose (LNT), lacto-N-neotetraose (LNnT), and optionally one or more excipients;
    increasing in the gastrointestinal microbiota of the non-infant human during the treatment period, the relative abundance of *Bifidobacterium adolescentis*; and
    reducing in the non-infant human during the treatment period, a precursor condition for a metabolic disorder associated with development of one or more of obesity-induced pre-diabetes and type 2 diabetes, the precursor condition selected from gut permeability, metabolic endotoxemia, low-grade metabolic inflammation, and body fat percentage.

9. The method of claim 8, wherein the reduced precursor condition for the metabolic disorder associated with development of the one or more of obesity-induced pre-diabetes and type 2 diabetes is gut permeability.

10. The method of claim 8, wherein the reduced precursor condition for the metabolic disorder associated with development of the one or more of obesity-induced pre-diabetes and type 2 diabetes is body fat percentage.

11. The method of claim 8, further comprising increasing, in the gastrointestinal tract of the non-infant human, a level of glucagon-like peptide selected from GLP-1 and/or GLP-2 relative to the level of the selected glucagon-like peptide prior to administering the single HMO.

12. The method of claim 8, wherein single synthetic HMO is administered in a unit dosage form.

13. The method according to claim 8, wherein the obese non-infant human is a prepubescent child.

14. The method of claim 8, wherein:
    the treatment period comprises an initial treatment phase and a maintenance phase;
    the effective amount of the selected HMO is from about 2.5 g to about 7.5 g daily during the initial treatment phase; and
    the effective amount of the selected HMO is from about 1 g to about 2.5 g daily during the maintenance phase.

15. A method comprising:
    administering to an obese non-infant human during a treatment period an effective amount of a mixture of two or more synthetic neutral human milk oligosaccharides (HMOs) selected from 2'-fucosyllactose (2'FL), 3-fucosyllactose (3-FL), difucosyllactose (DFL), lacto-N-fucopentaose I (LNFP-I), lacto-N-tetraose (LNT), and lacto-N-neotetraose (LNnT), and optionally one or more excipients;
    increasing in the gastrointestinal microbiota of the non-infant human during the treatment period, the relative abundance of *Bifidobacterium adolescentis*; and
    reducing in the non-infant human during the treatment period, a precursor condition for a metabolic disorder associated with development of one or more of obesity-induced pre-diabetes and type 2 diabetes, the precursor condition selected from gut permeability, metabolic endotoxemia, low-grade metabolic inflammation, and body fat percentage.

16. The method of claim 15, wherein the reduced precursor condition for the metabolic disorder associated with development of the one or more of obesity-induced pre-diabetes and type 2 diabetes is gut permeability.

17. The method of claim 15, wherein the reduced precursor condition for the metabolic disorder associated with development of the one or more of obesity-induced pre-diabetes and type 2 diabetes is body fat percentage.

18. The method of claim 15, further comprising increasing, in the gastrointestinal tract of the non-infant human, a level of glucagon-like peptide selected from GLP-1 and/or GLP-2 relative to the level of the selected glucagon-like peptide prior to administering the single HMO.

19. The method of claim 15, wherein single synthetic HMO is administered in a unit dosage form.

20. The method of claim 15, wherein:
    the treatment period comprises an initial treatment phase and a maintenance phase;
    the effective amount of the selected HMO mixture is from about 2.5 g to about 7.5 g daily during the initial treatment phase; and
    the effective amount of the selected HMO mixture is from about 1 g to about 2.5 g daily during the maintenance phase.

* * * * *